United States Patent
Delmotte et al.

(10) Patent No.: US 6,965,014 B1
(45) Date of Patent: Nov. 15, 2005

(54) FIBRIN MATERIAL AND METHOD FOR PRODUCING AND USING THE SAME

(75) Inventors: Yves Delmotte, Tertre (BE); James Diorio, Antioch, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/566,019

(22) Filed: May 8, 2000

Related U.S. Application Data

(63) Continuation-in-part of application No. 09/386,198, filed on Aug. 31, 1999, now Pat. No. 6,461,325, which is a continuation-in-part of application No. 08/679,658, which is a continuation-in-part of application No. PCT/EP96/00160, filed on Jan. 16, 1995.

(51) Int. Cl.$^7$ .......................... A61K 35/14; A61K 38/00; C07K 1/00; C07K 14/00; C07K 16/00
(52) U.S. Cl. ....................... 530/382; 530/381; 530/350
(58) Field of Search .............................. 424/78.17, 101, 424/27, 423; 604/82, 191; 527/200; 427/243; 514/55, 2, 12; 536/20; 530/354, 350, 381, 382

(56) References Cited

U.S. PATENT DOCUMENTS

| | | | |
|---|---|---|---|
| 4,442,655 A | 4/1984 | Stroetmann | |
| 5,318,524 A | 6/1994 | Morse et al. | |
| 5,989,215 A | 11/1999 | Delmotte et al. | |

FOREIGN PATENT DOCUMENTS

| | | | |
|---|---|---|---|
| WO | WO 96/22115 | | 7/1996 |
| WO | WO 98/02098 | | 1/1998 |
| WO | WO 98/12274 | * | 3/1998 |
| WO | WO 99/29338 | | 6/1999 |
| WO | WO 01/54735 | | 8/2001 |

* cited by examiner

*Primary Examiner*—Robert A. Wax
*Assistant Examiner*—Robert B. Mondesi
(74) *Attorney, Agent, or Firm*—Senniger Powers; Janice Guthrie; Bell, Boyd & Lloyd

(57) ABSTRACT

This invention describes a bioerodible fibrin material which is obtained by mixing fibrinogen and thrombin reconstituted or diluted with a particular high tonic strength medium, free of calcium. Such a fibrin-based biomaterial develops a tight structure with thin fibers and small pore size suitable for use as an anti-adhesion barrier. In this invention, thrombin is no longer the variable which governs the tightness and the porosity of the fibrin material obtained, but still controls the clotting time. The mechanical behavior, high-water capacity, and releasable retention properties for therapeutic agents of this fibrin structure causes the fibrin material to be ideally suited for use as a drug delivery device, capable of delivering proteins, hormones, enzymes, antibiotics, antineoplastic agents and even cells for local and systemic treatment of human and non-human patients.

45 Claims, 10 Drawing Sheets

Delivery device : pressurized can

FIBRIN MATERIAL AND METHOD FOR PRODUCING AND USING THE SAME

RELATED APPLICATIONS

This is a continuation-in-part application of U.S. Ser. No. 09/386,198, filed Aug. 31, 1999 now U.S. Pat. No. 6,461,325, which is a continuation-in-part of U.S. Ser. No. 08/679,658, now filed on Jul. 12, 1996, U.S. Pat. No. 5,989,215, which is a continuation-in-part of PCT application No. PCT/EP96/00160, filed Jan. 16, 1995, all of which incorporated herein by reference and made a part hereof.

TECHNICAL FIELD

This invention provides a fibrin hydrogel material and particularly a fibrin hydrogel useful as a drug delivery vehicle and for the prevention of post surgical adhesion.

BACKGROUND ART

One of the major problems in intra-abdominal surgery is the avoidance of post-operative adhesions. It is well-known that adhesions contribute to pain, immobility, retarded wound healing, and in particular to intestinal obstruction which even may be life-threatening. In the field of gynecological surgery, post-surgical adhesions involving female reproductive organs may result in infertility.

Each surgical procedure necessarily produces various forms of trauma where the abdominal cavity or other human cavity is opened for an inspection. Physiologically, the process of wound closure then starts when bleeding ceases upon formation of a hemostatic clot at the places where blood vessels are injured. The clot, at first comprising mainly platelets, is solidified by a fibrin network resulting from the activation of an enzyme cascade involving thrombin, factor XIII and calcium. Further steps on the way to the sealing of the wound are retraction of the hemostatic clot, invasion of various cell types including fibroblasts into the wound area and eventually the lysis of the fibrin network. Adhesions are thought to begin to form when the fibrin clot covering an injury comes into contact with a bleeding adjacent surface and the new connective tissue produced by the fibroblasts attach the two surfaces together.

The problems associated with adhesions often require a further operative procedure for removing/lysing the adhesions, called adhesiolysis, which, like the first operation, principally bears the risk of forming additional adhesions.

Accordingly, the prevention of adhesion formation is medically important. Among the different approaches for prevention of adhesion formation, one involves the use of materials as a physical or bio-mechanical barrier for the separation or isolation of traumatized tissues during the healing process. Both synthetic materials and natural materials have been used as a barrier to adhesion formation. Permanent, inert implants like Gore Tex® surgical membranes consisting of expanded polytetrafluoroethylene (PTFE) generally require a second operative procedure to remove them, while others such as surgical membranes of oxidized regenerated cellulose are biodegradable, but are thought to elicit an inflammatory response ultimately leading to adhesion formation (A. F. Haney and E. Doty, *Fertility and Sterility*, 60, 550–558, 1993).

Fibrin sealants and glues are well-known in the art for use in haemostasis, tissue sealing, and wound healing and have been commercially available for more than a decade. Use for anti-adhesion and drug delivery vehicle in glaucoma surgical procedures is one example. Fibrin glues mimic the last step of the coagulation cascade and are usually commercialized as kits comprising two main components. The first component is a solution comprising fibrinogen with or without factor XIII, while the second component is a thrombin calcium solution. After mixing of components, the fibrinogen is proteolytically cleaved by thrombin and thus converted into fibrin monomers. Factor XIII is also cleaved by thrombin into its activated form (FXIIIa). FXIIIa cross links the fibrin monomers to form a three-dimensional network commonly called "Fibrin Gel."

As disclosed in the commonly assigned published PCT patent application, WO 96/22115, a self-supporting sheet-like material of cross-linked fibrin material can be used as a bio-mechanical barrier in the treatment of internal traumatic lesions, particularly for prevention of adhesion formation as a post-operative complication. The '115 Application discloses the mixing of a thrombin and calcium containing solution with a fibrinogen and Factor XIII containing solution. By using high thrombin concentrations to catalyze the conversion of fibrinogen into fibrin, the resulting fibrin material was found to be sufficiently rigid to be self-supporting and to have sufficiently small pore size to prevent the ingress of fibroblasts which causes the formation of adhesions. The resulting fibrin material, however, did not readily retain water. In fact water could be easily expelled from the fibrin material by compressing the material by hand. Thus, this classic type fibrin material could not be used to deliver drugs to a wound site while being reabsorbed into the body during the fibrinolytic process.

This invention overcomes these and other shortcomings in the prior art devices. Hydrogel fibrin has a tight structure constituted of thin fibers defined by a low pore size. Water is trapped in the "void volume" of the structure. The "void volume" is small, regular, and homogenously distributed through the entire film material. Water cannot leave the film structure, due to its internal energy, and is released from the fibrin structure depending on the fibrinoytic rate of the biopolymer. The release of a drug incorporated into the water or buffer is regulated by passive diffusion and, depending upon the molecular weight, solubility and the fibrinolytic process.

The removal of calcium from the process of forming a fibrin structure yields no lateral associations of protofibrils. The lack of associations of protofibrils corresponds to a high number of thin fibers per unit of volume, thus conferring a tight pore size in the fibrin 20 structure. This tight pore size allows for water to remain trapped in the "void volume."

SUMMARY OF THE INVENTION

Other advantages and aspects of the present invention will become apparent upon reading the following description of the drawings and detailed description of the invention.

This invention provides a medical device for the prevention of post-surgical adhesion formation and the controlled release of drugs in human and non-human species. The device comprises a fibrin hydrogel material having a water content of at least about 90% by weight of the hydrogel. The fibrin hydrogel has a pore size within the range of less than 1 micron and preferably less than 0.1 $\mu$m has a transparency of less than about 1.0 AUFS, more preferably less than about 0.8 AUFS when measured with a spectrophotometer at 800 nm. The fibrin hydrogel is substantially free of cross-linking.

The present invention further provides a multilayer fibrin material for application to animal tissue. The characteristics of each layer are determined by the concentrations of the constituents and the presence of calcium and Factor XIII. In a preferred form, in addition to a fibrin hydrogel, the material or film includes one layer of a fibrin glue. The fibrin glue layer has a pore size within the range of less than 2 to 10 microns. In another embodiment, the fibrin hydrogel includes a layer of classic fibrin film. The classic fibrin film layer has a pore size within the range of 0.1 to 10 microns and is cross-linked.

In another embodiment, one layer of the multiple layer fibrin material is a therapeutic fibrin hydrogel material having a water content of at least 92.5% by weight of the hydrogel and whereby the hydrogel retains 90% of the water upon compression by a force from 1 to 14 psi. The therapeutic fibrin hydrogel layer of the multilayer fibrin material releasably retains a diluent whereby the diluent comprises a therapeutic agent. The therapeutic fibrin hydrogel layer of the multilayer fibrin material has a pore size within the range of 0.1 to 1 microns and has an optical clarity of less than about 1.0 AUFS, more preferably less than about 0.50 AUFS when measured with a spectrophotometer at 800 nm. The fibrin hydrogel layer is substantially free of cross-linking. In one embodiment of the therapeutic fibrin hydrogel layer of the multilayer fibrin material, the releasably retained therapeutic agent comprises a pharmaceutical compound. In another embodiment of the therapeutic fibrin hydrogel layer of the multilayer fibrin material, the releasably retained therapeutic agent comprises living cells, such as chondrocytes. Other cell types are contemplated as well.

DETAILED DESCRIPTION OF THE INVENTION

Figure 1:
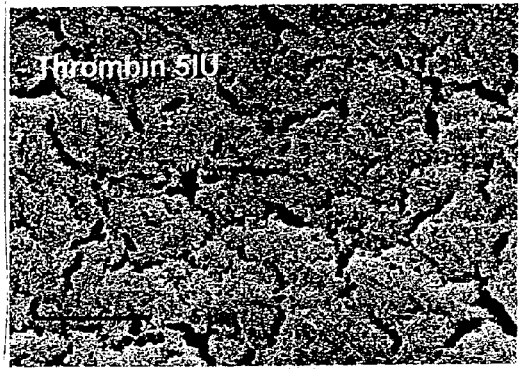
FIG. 1 depicts the fibrin hydrogel material prepared using the thrombin concentration of 5 IU.
Figure 2:
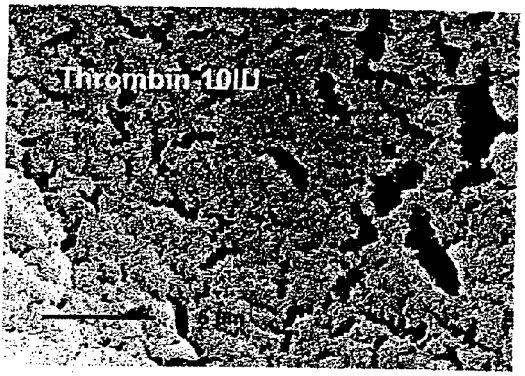
FIG. 2 depicts the fibrin hydrogel material prepared using the thrombin concentration of 10 IU.
Figure 3:
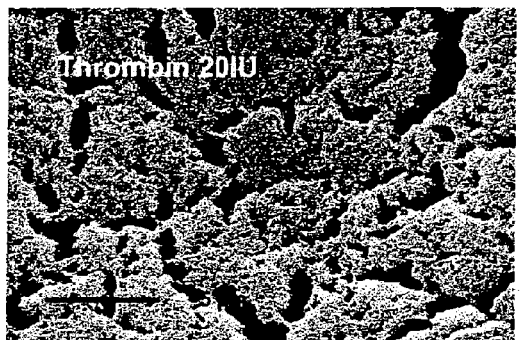
FIG. 3 depicts the fibrin hydrogel material prepared using the thrombin concentration of 20 IU.
Figure 4:
FIG. 4 depicts the fibrin hydrogel material prepared using the thrombin concentration of 100 IU.
Figure 5:
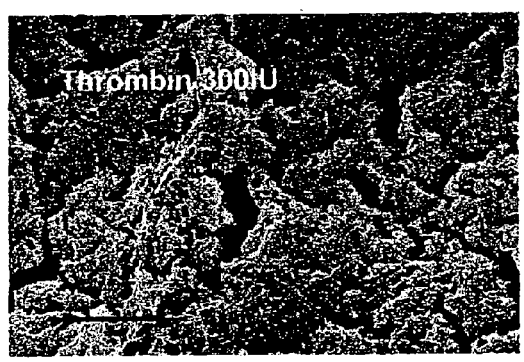
FIG. 5 depicts the fibrin hydrogel material prepared using the thrombin concentration of 300 IU.

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiments illustrated.

One preferred form of the present invention provides, a self-supporting, biodegradable, fibrin hydrogel material which is obtained by mixing fibrinogen and thrombin solutions diluted with a solute inhibiting the action of calcium on fibrinogen in a high ionic strength medium, both free of calcium. The prior art discloses that calcium is a critical component to forming a fibrin material. The resulting hydrogel material has thin fibers and small pore size and is suitable for use as an anti-adhesion barrier.

I. Fibrin Hydrogel Material

Preferably the fibrin hydrogel material for anti-adhesion applications will have a pore size from 1–5 microns, and more preferably from 0.1–3. The fibrin hydrogel material preferably also readily retains water upon compression. Preferably the hydrogel shall retain 80–90% of its water content upon compressing the material with a force from 1–14 psi.

The hydrogel material has a sufficiently high modulus of elasticity to be self-supporting. By self-supporting we mean that a fibrin hydrogel material of 5 cm long by 5 cm wide by 5 mm thick can be held at one end without the second end deflecting downward with respect to the held end more than 10 degrees.

It is also desirable that the fibrin hydrogel be relatively optically transparent and, in a preferred form, should have an optical density measured with a spectrophotometer at 800 nm of from 0.1–0.2, more preferably from 0.1–0.5 and most preferably from 0.1–0.4. As can be seen in FIG. 1, the fibrin hydrogel has a network of fibers 10 that should have an average diameter, in a preferred form, of less than about 5.0 microns, more preferably from less than about 2.0 microns and most preferably from less than about 1.0 microns or any range or combination of ranges therein.

In one preferred form of the invention, a fibrin hydrogel is a single layered material. The present invention further provides a multilayer fibrin material comprising two or more layers.

In preferred embodiments, the thickness of the fibrin barrier material is at least 200 µm when the barrier is in the wet state. Preferably the thickness is about 50 µm, and most preferably up to 10,000 µm, although it is believed that even material with a thickness of less than 100 µm may be suitable for the purposes of the invention.

The hydrogel material must also be capable of being reabsorbed into the body or be bioreabsorbable. Preferably, depending upon the concentration of fibrinogen and the quantity applied, a fibrin hydrogel of 3 cm×3 cm×1 cm the hydrogel will be reabsorbed into the body in its entirety by 14 days, more preferably within 10 days and most preferably within 5 days.

The fibrin hydrogel can be distinguished from classic fibrin material in several ways. First, the fibrin hydrogel can obtain a lower pore size than that of classic fibrin material with the same concentration of thrombin. The fibrin hydrogel has a tighter pore size regardless of the concentration of thrombin used. This has an advantage over classic fibrin materials in that the fibrinolytic process is maintained or increased over physiological levels.

Classic fibrin materials utilize large quantities of calcium, thus hampering the fibrinolytic process. The fibrinolytic process is slowed by the presence of gamma-gamma cross-links in the fibrin material, which are caused by the presence of excess calcium. The lower level of calcium in the fibrin hydrogel material inhibits cross-linking, thus allowing for a faster breakdown of the fibrin hydrogel material.

The increased time required by classic fibrin materials to be broken down may also result in a greater degree of adhesion. The anti-adhesion qualities of the fibrin hydrogel are believed to result from the thrombin content. The thrombin content of the fibrin hydrogel allows for a higher fibrinolytic rate than classic fibrin materials.

Another distinction is the fibrin hydrogel's ability to retain water under compression forces. The degree of water retention in the fibrin hydrogel greatly exceeds the water retention of the classic fibrin materials. This permeability factor is a primary distinction between the fibrin hydrogel of the present invention and classic fibrin materials. The slow rate of water release by the fibrin hydrogel material allows the hydrogel to act as a lubricant by release of water, further enhancing its anti-adhesion properties.

II. Method of Forming a Fibrin Hydrogel

It has been found by the present inventors that a fibrin hydrogel material may be formed in the absence of a calcium containing solution and in the absence of a Factor XIII containing solution which were previously considered in the art to be essential components. In a preferred form of the invention a fibrin hydrogel is obtained by admitting a fibrinogen-containing solution with a thrombin-containing solution. The fibrinogen solution should have from 1.5–100 mg/ml, more preferably 3–70 mg/ml and most preferably a 45 mg/ml fibrinogen dissolved in a solution containing components capable of chelating calcium. The chelating component should also be non-toxic and in a preferred form of the invention is a phosphate buffer saline solution (PBS) of physiologically acceptable levels. The chelating agent should be an antagonist to fibrinopeptide transmidation reaction 5 IU-300 IU.

Also, contrary to the teachings in the prior art, the thrombin concentration of the admixed components does not determine the pore size of the hydrogel fibrin material. As will be discussed below and as shown in FIGS. 1–5, fibrin hydrogel materials were formed having relatively the same pore size notwithstanding the use of thrombin concentrations from 1 IU to 300 IU. The concentration of thrombin was still found to control the rate of forming a fibrin hydrogel.

It is well known that mixing a first solution containing fibrinogen with Factor XIII and a second solution of thrombin with calcium will result in the formation of a fibrin material with pronounced lateral association and considerable cross-linking among its thick fibers. It is also well known that thrombin acts as a protease which will cleave fibrinopeptide A and B from the fibrinogen molecule and convert it into fibrin. The fibrinopeptides of vertebrate species reportedly have a large net negative charge. The presence of these and other negatively charged groups in the fibrinopeptides are likely actors in keeping fibrinogen apart. Their release by thrombin gives fibrin monomers a different surface-charge pattern, leading to their specific aggregation.

In particular, removal of the fibrinopeptides changes the net charge of the central globular unit from −8 to +5. Each of the terminal globular units has a net charge of −4. Thus, electrostatic interactions between the terminal and central globular units probably stabilize the structure of fibrin.

It is also known that calcium ions play an important role in the dissociation of Factor XIII subunit A from Factor XIII subunit B as Factor XIII is converted to its activated form, Factor XIIIa. Furthermore, it is know that Factor XIIIa is critical to the cross-linking of fibrin monomers. It is also known that the widths of the fibers comprising the fibrin material can be decreased by increasing the pH and ionic strength of the diluents.

By removing (chelating) calcium ions bound to fibrinogen, the inventors have been able to modify the fibrin structure to obtain further embodiments of the fibrin hydrogel. Accordingly, the present invention uses a solution capable of scavenging calcium ions associated with the fibrinogen molecules. In a preferred form of the invention, a phosphate buffer solution having a concentration similar to physiologically acceptable levels. The inventors suggest that the resulting structural modifications of the fibrin hydrogel occur as a result of a "charge effect" which alters the aforementioned electrostatic interactions between the terminal and central globular units, thereby inhibiting the lateral association of fibrin. In further embodiments of the fibrin hydrogel, modification of Factor XIII concentration used in the synthesis of fibrin alters the crosslinking characteristics of the final fibrin material. Thus, in further embodiments of the invention, the inventors have developed a fibrin hydrogel that can be synthesized with low concentrations of thrombin and according to the end user's specifications as to the lateral association and fiber thickness of the resulting fibrin hydrogel structure.

During the formation of a fibrin hydrogel, it is desirable that all of the fibrinogen be converted into fibrin, as residual amounts of fibrinogen may lead to adhesion formation upon reacting with thrombin present in the body. Accordingly, in still further embodiments of the present invention, the fibrin hydrogel further comprises less than 5% by weight of fibrinogen, preferably less than 4% by weight of fibrinogen, preferably less than 3% by weight of fibrinogen, preferably less than 2% by weight of fibrinogen, and most preferably less than 1% by weight of fibrinogen, in terms of the total dry weight of the fibrinogen plus fibrin each time. For the purpose of determining the fibrin and the fibrinogen content of the fibrin film, the methods of SDS-Page (SDS-Gel Electro-phoresis) may be used.

Figure 6:
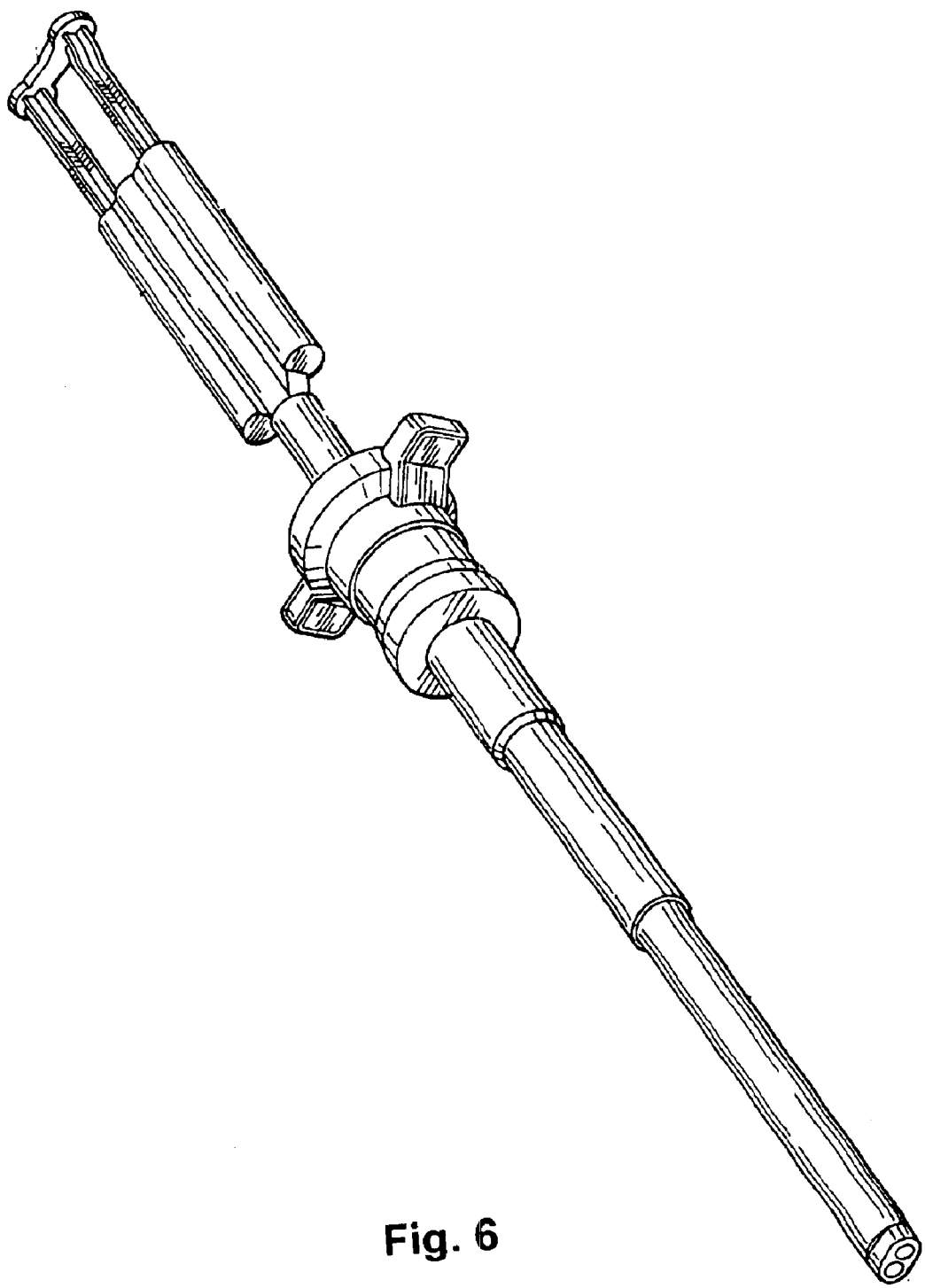
FIG. 6 depicts a medical device that may be used to, form the fibrin hydrogel material inside and outside the animal body.

The medical devices shown in FIG. 6 and as further described in commonly assigned U.S. Pat. No. 5,989,215 may be used topically, in open-type surgeries (for example, laparotomic surgeries) or minimally invasive surgeries (for example, laparoscopic surgeries). Of course, there are other types of open-type surgeries and minimally invasive surgeries as will be appreciated by one of ordinary skill in the art. The medical device 20 may be used to form fibrin hydrogel material inside and outside the animal body.

The present invention provides a process for preparing a self-supporting fibrin hydrogel matrix or film outside the body comprising the steps of:

(a) mixing a stream of a first, fibrinogen-containing solution dissolved in PBS with a stream of a second, thrombin-containing PBS solution;

(b) applying the obtained mixture to a solid support or mixing the components of the solid support; and (c) incubating the mixture to form the hydrogel matrix.

In order to obtain a mixture as homogenous as possible (and thus a homogenous final product) in step (a) a stream of a first, fibrinogen-containing solution is mixed with a stream of a second, thrombin-containing solution by simultaneous delivery of the components. It is also possible to deliver one component to a surface followed by the other component. Preferably, equal volumes of the first and the second solution are mixed. In case the different volumes of the first and the second solution should be mixed, it will be known in the art which measures have to be taken in order to ensure that a homogenous mixture is obtained.

Using the delivery device mentioned above, the resulting mixture is spread over the surface of a solid support, for example a petri dish or the like, which is tilted to cover the entire surface as far as possible before the formation of the fibrin hydrogel material begins.

For the purpose of preparing a fibrin hydrogel on mammal tissue, the inventors propose a process comprising the steps of:

(a) providing a first phosphate buffer solution containing fibrinogen;

(b) providing a second phosphate buffer solution containing thrombin;

(c) mixing the first solution and the second solution before or after placing the mixture on an animal tissue;

(d) and obtaining a fibrin hydrogel material with a tight structure and small pore size suitable for post-surgical adhesion prevention.

The fibrinogen and thrombin solutions can be initially mixed in a delivery device, or be atomized into a spray and mixed while in the form of spray droplets while in mid air or upon first making contact with the tissue surface or delivered through a multi-lumen catheter.

The fibrin hydrogel may be formed by utilizing constituents of a kit. A preferred embodiment of the fibrin hydrogel kit includes:

(a) a vial of proteins including fibrinogen;

(b) a vial of thrombin;

(c) a vial of phosphate buffer solution to serve as a diluent; and (d) appropriate ancillary mixing and application apparatus, including, but not limited to syringes and catheters.

One further embodiment of the fibrin hydrogel kit includes a vial containing the protein cocktail where the protein content is no less than 30 mg/ml. Another further embodiment of the fibrin hydrogel kit includes a vial containing the protein cocktail where the Factor XIII content ranges from 0 IU/ml to 80 IU/ml. Yet a further embodiment of the fibrin hydrogel kit includes a vial containing thrombin, where the concentration of thrombin ranges between 0.1 IU/ml to 1000 IU/ml. In yet another preferred embodiment of the fibrin hydrogel kit, the constituents supplied are pre-formulated to ensure that when mixed, the hydrogel achieved will have a homogeneous structure with tight pore sizes suitable to act as a prophylaxis to adhesion formation.

Figure 7:
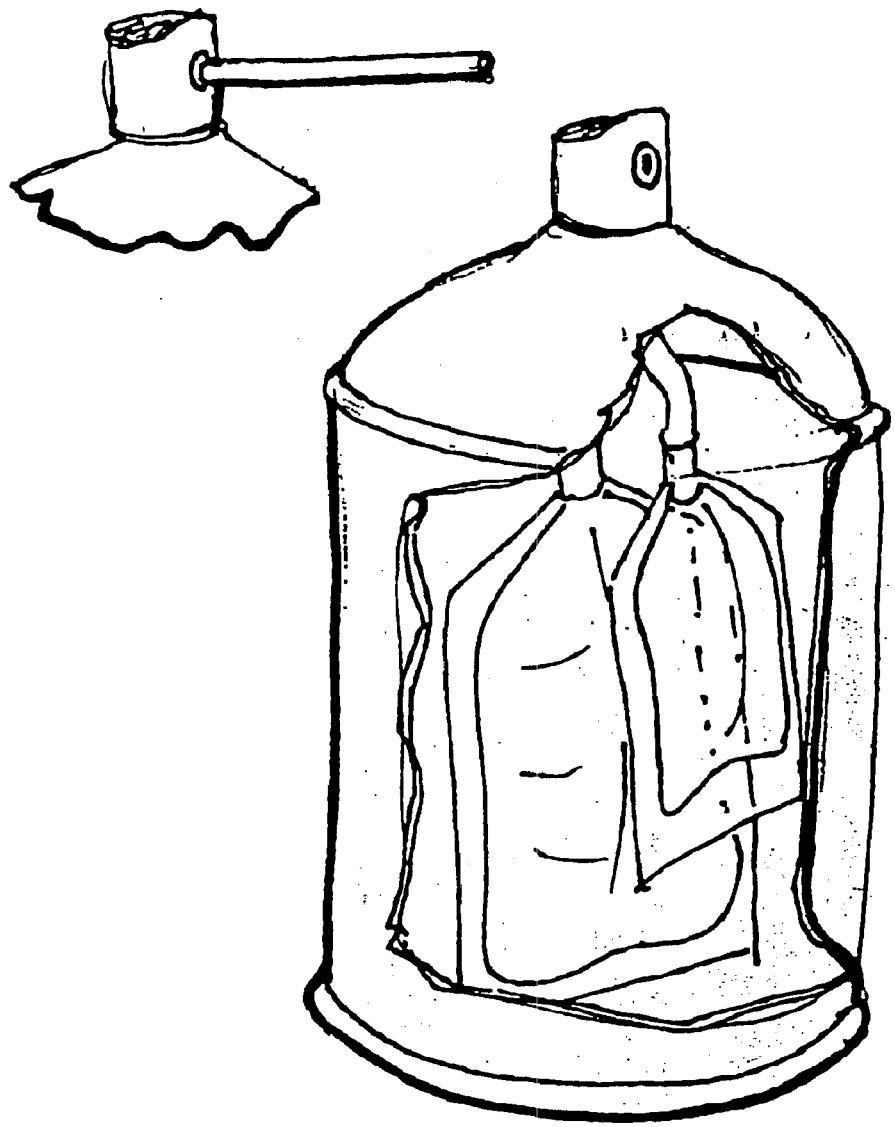
FIG. 7 depicts a pressurized canister housing fibrinogen and thrombin as powders in separate bags.
Figure 8:
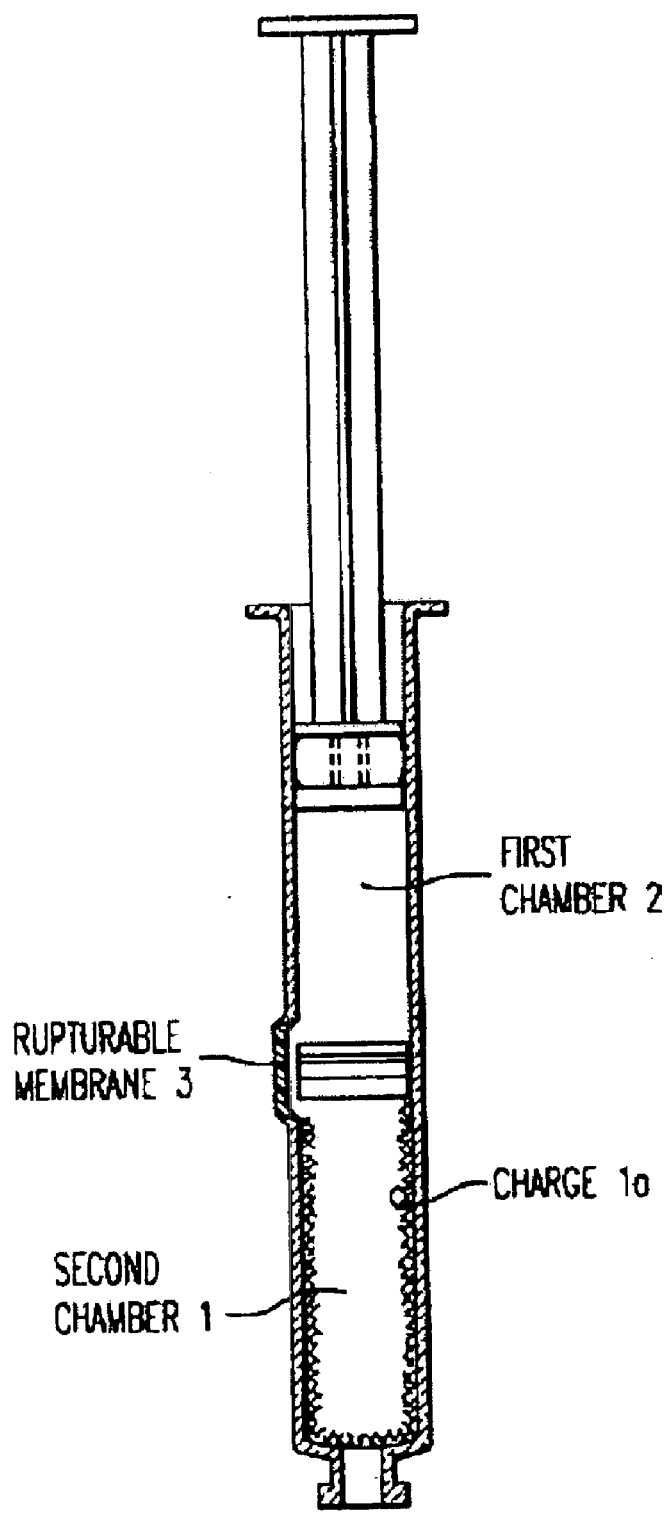
FIG. 8 depicts a double syringe system housing fibrinogen and thrombin in separate chambers.

Another preferred embodiment of the fibrin hydrogel kit includes pre-formulated constituents, supplied to ensure that when mixed, the hydrogel achieved will have a homogeneous structure with tight pore sizes suitable to act as a prophylaxis to adhesion formation and as a drug delivery system. A lack of adhesion can be seen with in fibrinogen free of FXIII or similar acting component. The fibrin hydrogel kit includes a vial of fibrinogen mixed with inactivated thrombin, a vial of suitable buffer, an ancillary, a device equipped with optical fiber to photoactivate the thrombin, and a light supply. In another preferred embodiment of the fibrin hydrogel kit, the fibrinogen, inactivated thrombin, suitable buffer, and an ancillary are all in one delivery device. FIG. 7 illustrates another preferred embodiment where a pressurized canister houses fibrinogen and thrombin as powder in separate bags. The canister may be unscrewed to allow for rehydration of the fibrinogen and thrombin. Increasing the pressure allows both components to be sprayed through a double tube system or through concentric channels. Another preferred embodiment, FIG. 8, utilizes a double syringe system with volumes of less than 100, 50, 20 ml each, more preferably less than 20 ml each, and most preferably less than 10 ml each, but greater than 3.0 ml. This double syringe system is equipped with a Y-shaped connection to incorporate a tube. Such devices can be used for veterinary applications. In another preferred embodiment, the fibrin hydrogel material can be fabricated into articles selected from the group consisting of films, tubes, and pellets. These fibrin hydrogel materials can be fabricated into articles using techniques selected from the group of extrusion, molding, and thermal forming. These fibrin hydrogel materials can be sterilized at a temperature below 0° C. by gamma radiation, stored at a temperature below 0° C., and used upon demand. The sterilization by gamma radiation is below −25° C., at a dosage of at least 25 kGy. In yet another preferred embodiment of the fibrin hydrogel kit, the vial of diluent contains a phosphate buffer solution. In another preferred embodiment of the fibrin hydrogel kit, the vial of diluent contains a high-ionic strength buffer capable of scavenging the fibrinogen-linked calcium. Other suitable solutions include; sodium citrate, potassium citrate, EDTA, EGTA, chloride solutions, phosphate solutions, or other ions solutions having a strong affinity for calcium. Fibrinogen, thrombin, and other proteins such as fibronectin and FXIII may be from a single donor, multiple donors, pooled donors, Cohn I fraction, or recombinant.

In another preferred embodiment of the fibrin hydrogel kit, the vial of diluent contains a buffer capable of chelating exogenous calcium.

III. Therapeutic Fibrin Hydrogel

The present invention further provides a fibrin hydrogel that releasably retains a diluent or a therapeutic agent. The therapeutic agent is retained within the pores of the hydrogel material and when placed into the body of a mammal is released over time as the fibrin hydrogel is reabsorbed into the body.

The therapeutic agent(s) that are contemplated to be releaseably retained by the therapeutic hydrogel layer comprises, but is not limited to, pharmaceutical compounds, antibiotics, fibrinolytic agents, and biological response modifiers, in particular cytokines and wound repair promoters, preferably in an amount up to 1% by weight in terms of the total dry weight of fibrin plus fibrinogen. Due to the chemotactive properties of thrombin, low thrombin concentration is preferred for the purpose of anti-adhesion. However, higher concentrations of thrombin may be required to hasten clotting time. Clotting time was performed with a semi-automated BFT II device from Dade Behring on fibrinogen at 25 mg/ml with varying thrombin concentrations of 0.5, 1.0, 2.5, 5.0, and 10.0 IU/ml. PBS was used as a diluent for fibrinogen and thrombin. The clotting times are listed in the table below.

| Fibrinogen Concentration | Thrombin Concentration | Clotting Time (Seconds) |
|---|---|---|
| 25 mg/ml | 0.5 IU/ml | 430 |
| 25 mg/ml | 1.0 IU/ml | 237 |
| 25 mg/ml | 2.5 IU/ml | 83 |
| 25 mg/ml | 5.0 IU/ml | 37 |
| 25 mg/ml | 10.0 IU/ml | 20 |

Examples of fibrinolytic agents include t-PA, $\mu$-PA, streptokinase, staphylokinase, plasminogen and the like. These compounds promote fibrinolysis and thus can be used for controlling the rate of the degradation of the fibrin film in vivo. The term "biological response modifiers" is meant to refer to substances which are involved in modifying a biological response, such as wound repair, in a manner which enhances the desired therapeutic effect. Examples include cytokines, growth factors, and the like. Due to its intrinsic mechanical properties, the fibrin film of the invention does not require any additional cross-linking agent which may exert any toxic effects to the human or animal body. Due to its high level of dilution, it is possible for the fibrin hydrogel to trap and release water. This is useful for the hydration of tissues or as a lubricant to assist in the anti-adhesive properties of the fibrin hydrogel.

The therapeutic agent can be incorporated into the fibrin hydrogel material during the formation of the hydrogel. The therapeutic agent may either water soluble or water insoluble, antibody, antimicrobial agent, agent for improving biocompatability, proteins, anti-inflammatory compounds, compounds reducing graft rejection, living cells, cell growth inhibitors, agent stimulating endothelial cells, antibiotics, antiseptics, analgesics, antineoplastics, polypeptid es, protease inhibitors, vitamins, cytokines, cytotoxins, minerals, interferons, hormones, polysacharides, genetic material, growth factors, cell growth factors, substances against cholesterol, pain killers, collagens, stromal cells, osteo-progenitor cells, polylactate, alginate, $C_2$–$C_{24}$ fatty acids, and mixtures thereof. The delivery of the therapeutic agent regulated by either or both the passive diffusion and the fibrinolytic rate. The therapeutic agent can be dissolved in one or both of the thrombin or fibrinogen solutions. The therapeutic agent is retained by the hydrogel material as it forms out of the admixed solution.

IV. Multilayer Fibrin Hydrogel Film

The present invention further provides a multiple layer fibrin hydrogel film. The fibrin hydrogel can include a single additional layer or multiple additional layers of fibrin glue, classic fibrin film, fibrin hydrogel, therapeutic fibrin hydrogel film and layers of other synthetic or naturally occurring materials, such as alginate, polylactic, glycolic, silicon, and hyluronic compounds. The present invention contemplates this material being bound to the surface of synthetic polymers by modifying the surface biomechanically or otherwise altering the physical retention of the surface. Additionally, partially premixing the components at the interface between the layers may allow for bonding to occur. Furthermore, binding to collagen or other organic material is also contemplated. Collagen and other organic materials have a chemical affinity for proteins such as fibrinogen and fibronectin. The present invention contemplates selecting any combination of the above components and connecting them together in differing orders based upon the desired function of the film material. The present invention further contemplates selecting the individual thicknesses of the individual layers and the overall thickness of the film based upon its intended function. The following is a set of non-limiting examples of multiple layered films. The present invention should not be limited to these exemplary embodiments.

The present invention provides a multiple layered fibrin film having a first layer of a fibrin hydrogel or therapeutic hydrogel and a second layer of a classic fibrin film. The "classic" fibrin film is obtained by mixing a thrombin and calcium containing solution with a fibrinogen and Factor XIII containing solution as disclosed in detail in PCT Application WO 96/22115 which is incorporated herein by reference and made a part hereof. The first and second layers readily adhere to one another. During the conversion process, the adhesive property of fibrinogen is present and can allow the layers to stick together. If the fibrinogen is added too late, the obtained fibrin material is no longer adhesive, thus resulting in the possibility of delamination. It is contemplated by the present invention that mechanical retention can be inhanced by making holes in the first layer where the fibrin glue can penetrate and adhere the layers.

The present invention also provides a three-layered film having a first layer of a fibrin hydrogel, an inner layer of fibrin glue and an outer layer of a therapeutic hydrogel material. Another three-layered film includes inner and outer layers of fibrin glue on opposed surfaces of a layer of fibrin hydrogel material. Preferably the fibrin glue is obtained by mixing of fibrinogen-containing solution with an equal volume of a thrombin-containing solution. The fibrinogen-containing solution contains fibrinogen and factor XIII (0.1–40 IU/ml). The concentration of fibrinogen is expressed as the total protein concentration (preferably from about 3–140 mg/l and more preferably 30–110 mg/ml) and the percentage of clottable protein therein.

It is also preferred that the fibrinogen solution have a viscosity that allows the solution to be sprayed and preferably sprayed using pressures generated using a hand-operated syringe. The fibrinogen solution should have a viscosity of less than 20 centipoise, more preferably less than 10 centipoise, and most preferably from 1–5 centipoise or any combination or subcombination of ranges therein. The thrombin-containing solution should To have a thrombin concentration less than 10000 IU thrombin. The fibrin glue has been preferably made by mixing said fibrinogen-containing solution with an equal volume of a thrombin-containing solution of at least 50 IU thrombin, preferably of at least 150 IU thrombin, and most preferably of at least 300 IU thrombin.

Yet another example of a multilayered film includes layers stacked in the order of classic fibrin film/hydrogel/therapeutic hydrogel/hydrogel/classic fibrin film. In this case the delivery of the therapeutic agent in the therapeutic hydrogel can be delayed by the time it takes for the outer layers to be reabsorbed into the body. Thus, the present invention provides for building into the structure of the multilayered film time delivery sequences or schemes as desired.

Other contemplated embodiments include:
1. A multilayered structure composed of a surface layer of hydrogel material and a bottom layer of membrane. The membrane may be tissue or fibrin.
2. A multilayered structure composed of a surface layer classic fibrin and a bottom layer of hydrogel material.
3. A multilayered structure composed of outer layers of classic fibrin and an inner layer of hydrogel material.
4. A multilayered structure composed of a surface layer of hydrogel material and an inner layer of fibrin sponge material.

5. A multilayered structure composed of outerlayers of hydrogel material and an inner layer of membrane.
  6. Beads of hydrogel material between 0.1 mm and 3 mm.
  7. A hydrogel material anatomically molded.

The present invention also provides a process for preparing a multilayer fibrin material. One such process for preparing a multilayer fibrin material includes the steps of:
  (1) providing a base fibrin hydrogel layer, comprising the steps of:
    (a) providing a first buffer solution containing fibrinogen;
    (b) providing a second buffer solution containing thrombin;
    (c) providing additional constituents in either the first or second buffer solutions as required for a specific preparation;
    (c) mixing the first solution, the second solution, and any additional solutions on a surface such as a petri dish or tissue;
    (d) and obtaining a fibrin layer with a desired structure and desired pore size suitable for its designated purpose.
  (2) providing an additional layer by repeating steps 1(*a*) through 1(*d*) wherein the mixing occurs on the earlier formed layer or layers;
  (3) providing additional layers, if desired, by repeating step 2;
  (4) providing a final layer by repeating steps 1(*a*) through 1(*d*).

The present invention further provides a fibrin hydrogel that retains a higher proportion of water than fibrin materials currently available. The greater degree of water retention is particularly beneficial to the therapeutic use of the hydrogel. The retention of water is necessary for the control of the concentration of therapeutic agents contained within the fibrin hydrogel, as well as for the effective release of these therapeutic agents and additives.

The ability of fibrin hydrogels to retain water while being subjected to compression forces was tested and compared to the water retaining capacity of a classic fibrin material. In particular, compression was applied by centrifugation of the materials at various rotational speeds and the amount of water retained was measured. A refrigerated centrifuge (Sorvall RT 6000B) spun fibrin hydrogels at different speeds:
  1000 rpms for 30 min. corresponding to 156G
  2000 rpms for 30 min. corresponding to 625G
  3000 rpms for 30 min. corresponding to 1428G Amicon filter type "centricon 30" was used, corresponding to a membrane cutoff of 30000 and characterized by a maximum rotation time of 30 min and sustaining a G-force max of 5000G. The Amicron filter is composed of two units. The upper unit contains the filter component itself and can be attached to the second unit of the Amicron filter. The second, or lower, unit is the bottom cup. The bottom cup allows for the collection of water that is expelled from the fibrin material deposited on the filter of the upper unit. The water collected in the bottom cup is used to measure the amount of water released by the fibrin materials at the various rotational speeds. Once fibrinogen and thrombin solutions were prepared, a volume of approximately 1 ml of fibrin was applied to the filter. An appropriate mixing device is required for the fibrinogen and thrombin mixture to be complete and homogeneous.

Upper and lower parts are separately weighed before the fibrin material deposition and after each centrifugation step. A correction factor is calculated in order to consider that 1 g of fibrin has been distributed on the filter.

Separate experiments were conducted to test the effects of diluents. The procedural steps for each experiment went as follows:
  1) The filter and the bottom cup of the Amicon filter are separately weighed, then the fibrin material obtained by mixing each fibrinogen solution with a 20 IU/mL thrombin solution is put on the filter.
  A correction factor is calculated in order to consider that 1 g of fibrin has been distributed on the filter.
  The filter is centrifuged at 1000 rpm for 30 minutes.
  At the end of the centrifugation cycle, the bottom cup is carefully removed, weighed and recorded.
  2) The bottom cup is connected to the filter and centrifuged at 2000 rpm for 30 minutes, at the end of the cycle, the bottom cup is weighed and the cumulative value recorded.
  3) Again the bottom cup is connected to the filter and centrifuged at 3000 rpm for 30 minutes and the bottom cup weighed at the end of the cycle.

In the first experiment, the fibrinogen vial was reconstituted with 3.5 ml- distilled water to obtain a final concentration of 100 mg/ml of fibrinogen. Dilutions of the fibrinogen were performed with water in order to respectively obtain:
  dilution 1:2 (50 mg/ml) in water
  dilution 1:4 (25 mg/ml) in water
  dilution 1:6 (16.6 mg/ml) in water
  dilution 1:8 (12.5 mg/ml) in water Thrombin (Baxter Hyland) was reconstituted with 3.5 ml of 40 mmol $CaCl_2$ in order to obtain a concentration of 300 IU/mL. A dilution is performed with $CaCl_2$ to obtain a thrombin concentration of 20 IU/mL.

Fibrinogen solutions were then mixed with an equal volume of thrombin (20 IU/mL) to obtain a final concentration of "fibrinogen" respectively of:
  Sample 1: diluted 1:4 (25 mg/ml)
  Sample 2: diluted 1:8 (12.5 mg/ml)
  Sample 3: diluted 1:12 (8.3 mg/ml)
  Sample 4: diluted 1:16 (6.25 mg/ml)

Figure 11:
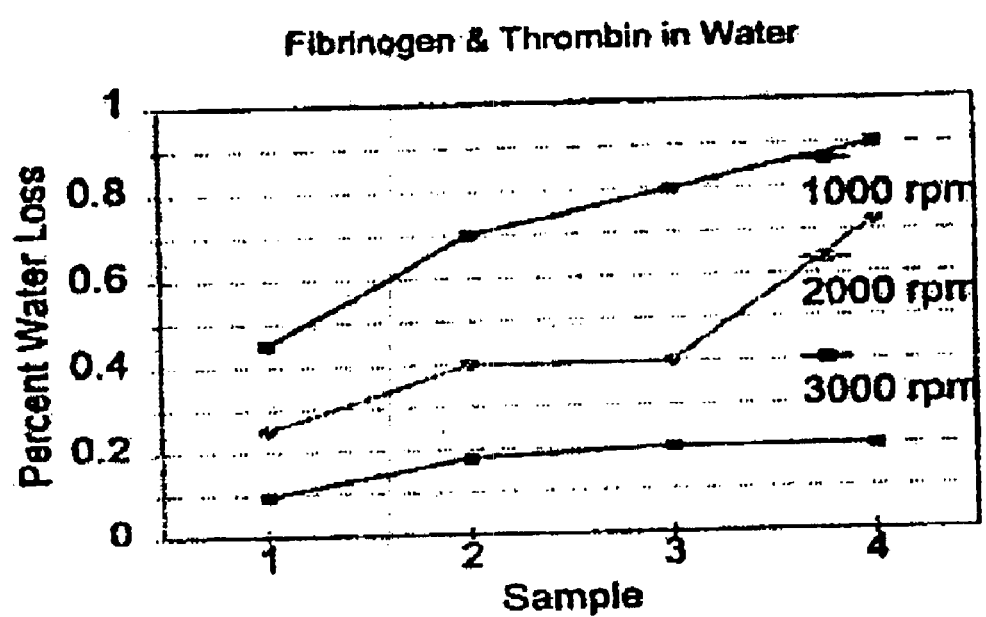
FIG. 11 is a chart depicting the percent water loss for 4 samples of fibrinogen solutions that were mixed with equal volumes of thrombin.

For sample 1, the loss of water was 9.5%, 25%, and 45% at 1000, 2000, and 3000 rpm respectively. Sample 2 showed a loss of water of 18%, 40%, and 70% at 1000, 2000, and 3000 rpm respectively. The loss of water in sample 3 was 20%, 40%, and 80% at 1000, 2000, and 3000 rpm respectively. Sample 4 expressed a water loss of 20%, 72%, and 90% at 1000, 2000, and 3000 rpm respectively. See FIG. 11.

The second experiment was a comparison of water retention between fibrin obtained by mixing fibrinogen and thrombin respectively reconstituted and diluted in PBS and fibrinogen reconstituted and diluted in PBS with thrombin reconstituted and diluted in 40 mmol calcium chloride.

In these comparisons, a vial of fibrinogen was reconstituted with 3.5 ml PBS (phosphate buffered saline pH=7.2) to reach a final concentration of 100 mg/mL of fibrinogen.

Dilutions were performed from this vial in order to obtain fibrinogen concentrations of:
  Sample 1 1:2 (50 mg/ml) in PBS
  Sample 2 1:4 (25 mg/ml) in PBS
  Sample 3 1:6 (16.6 mg/ml) in PBS
  Sample 4 1:8 (12.5 mg/ml) in PBS In th experiment depicted in FIG. 12A, thrombin (Baxter Hyland) was reconstituted with 3.5 mL of PBS in order to obtain a concentration of 300 IU/mL. A dilution was performed with PBS to obtain a thrombin concentration of 20 IU/mL.

Figure 12A:
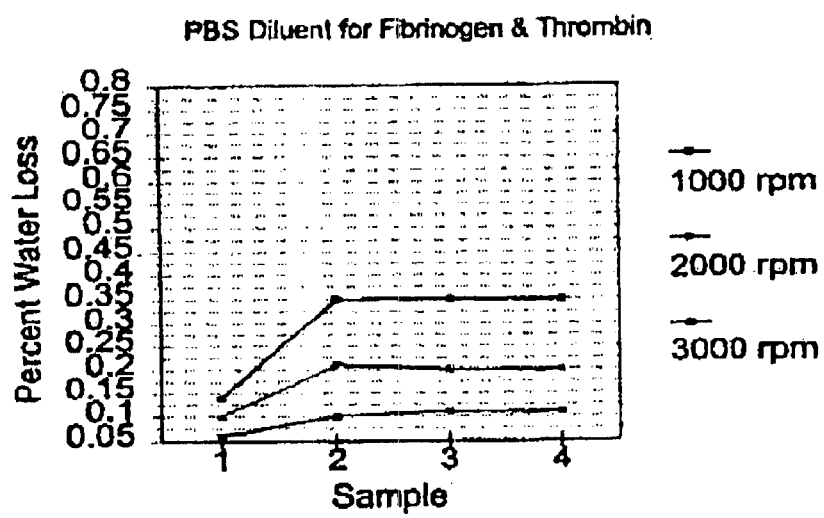
FIG. 12A is a chart depicting the percent water loss for 4 samples of fibrinogen and thrombin solutions diluted in PBS.
Figure 12B:
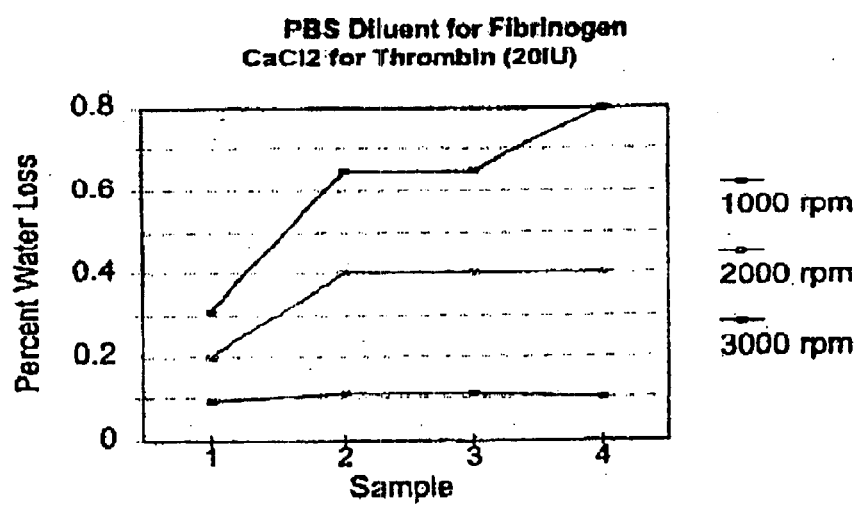
FIG. 12B is a chart depicting the percent water loss for 4 samples of fibrinogen and thrombin solutions wherein the fibrinogen is diluted in PBS and the thrombin is diluted in $CaCL_2$.

In the experiment depicted in FIG. 12B, thrombin (Baxter Hyland) was reconstituted with 3.5 ml of 40 mmol CaCl2 (calcium chloride) in order to obtain a concentration of 300 IU/mL. A dilution was performed with CaCl2 to obtain a thrombin concentration of 20 IU/mL.

The fibrinogen solutions were then mixed with an equal volume of thrombin (20 IU/mL), resulting in final concentrations for fibrinogen of:

Sample 1: diluted 1:4 (25 mg/ml) in PBS
Sample 2: diluted 1:8 (12.5 mg/ml) in PBS
Sample 3: diluted 1:12 (8.3 mg/ml) in PBS
Sample 4: diluted 1:16 (60.25 mg/ml) in PBS For the experiment depicted in FIG. 12A, sample 1 expressed a loss of water that was 6%, 10%, and 14% at 1000, 2000, and 3000 rpm respectively. Sample 2 showed a loss of water of 10?%, 21%, and 35% at 1000, 2000, and 3000 rpm respectively. The loss of water in sample 3 and 4 was nearly identical at 11%, 20%, and 35% at 1000, 2000, and 3000 rpm respectively. See FIG. 12A.

The introduction of calcium to the fibrin formulation through the diluent used for the thrombin dilutions in the experiment depicted in FIG. 12B directly affected the water retention. The loss of water was not significant at 1000 rpm for the samples, but water losses increased significantly to approximately 40% at 2000 rpm for samples 2 through 4. At 3000 rpm, water loss increased to approximately 65% for samples 2 and 3. A water loss of 80% for sample 4, similar to the result obtained for fibrin described in experiment 1, was recorded at 3000 rpm. The results for these experiments support the hypothesis that fibrin structures essentially free of calcium ions are also tighter, more compact, and have a greater resistance to water loss from compression forces. See FIG. 12B.

Figure 13A:
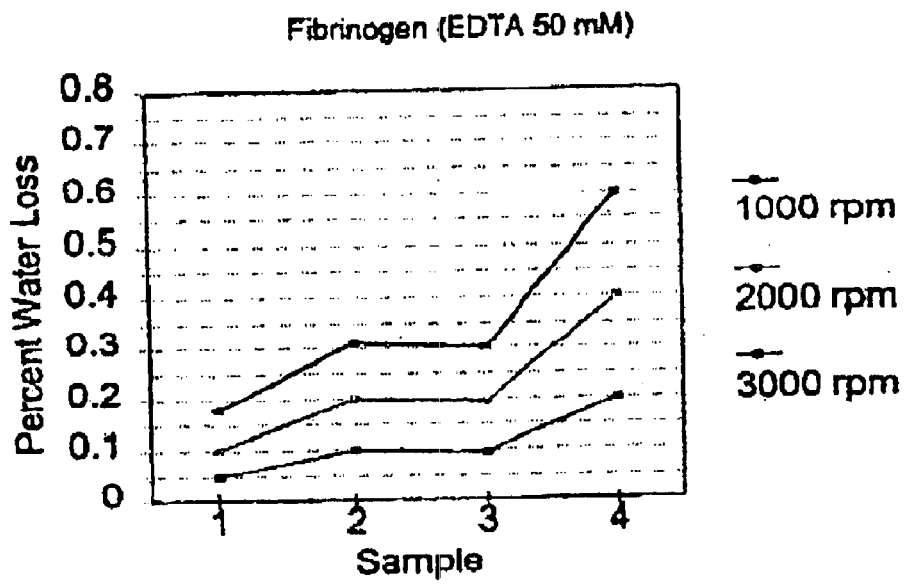
FIG. 13A is a chart depicting the percent water loss for 4 samples of fibrinogen and thrombin solutions diluted in EDTA.
Figure 13B:
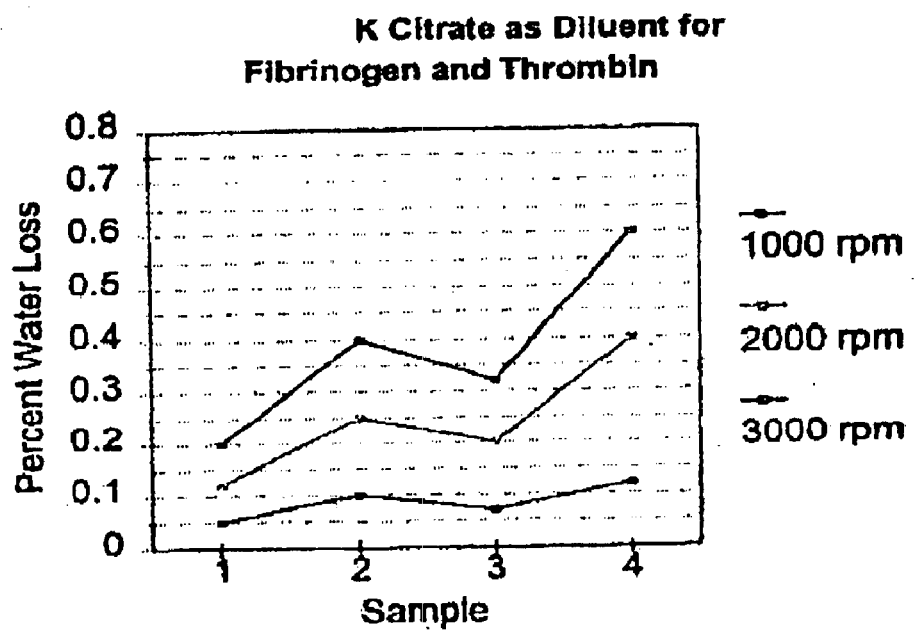
FIG. 13B is a chart depicting the percent water loss for 4 samples of fibrinogen and thrombin solutions diluted in potassium citrate.

As a means of verification for the role of phosphate as a complexing agent of the remaining calcium ions on fibrinogen molecules, reproductions of the PBS experiment above were conducted substituted EDTA for PBS in one trial, and citrate of potassium for PBS in a second trial. The patterns of water loss for both the EDTA and citrate of potassium trials were consistent with the results from the experiment utilizing PBS as a reconstitution agent. See FIGS. 13A and 13B. These results sustain the hypothesis that remaining calcium on fibrinogen reacts with phosphate ions preventing the collateral association of protofibrils producing a tight fibrin structure more resistant to water loss than fibrin structures retaining calcium.

Another experiment was conducted to determine the impact of the FXIII present in the formulation on the compaction capability of the fibrin material obtained with PBS as diluent for both fibrinogen and thrombin. In this experiment, a vial of fibrinogen (Tisseel from Baxter Hyland-Immuno lot P5488797D) is reconstituted with 4.0 ml of PBS (dilution 1:2) to reach a final concentration of 50 mg/mL of fibrinogen.

Figure 14:
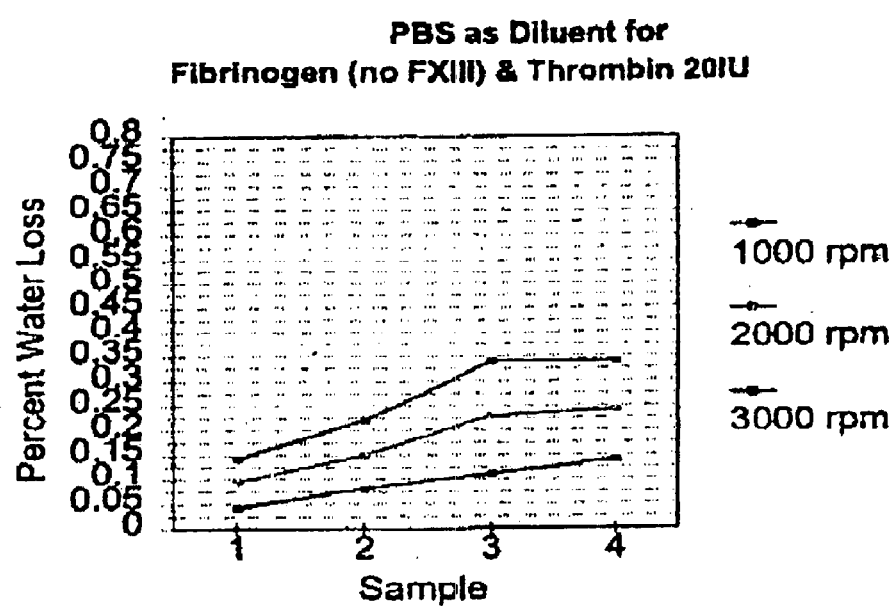
FIG. 14 is a chart depicting the percent water loss for 4 samples of fibrinogen, which is free of FXIII and thrombin diluted in PBS.

Dilutions are performed from this vial in order to obtain a fibrinogen concentration respectively of:

Dilution 1:2 (50 mg/ml) in PBS
Dilution 1:4 (25 mg/ml) in PBS
Dilution 1:6 (16.6 mg/ml) in PBS
Dilution 1:8 (12.5 mg/ml) in PBS Thrombin (Baxter Hyland) is reconstituted with 3.5 mL of PBS in order to obtain a concentration of 300 IU/mL. A dilution is performed with PBS to obtain a thrombin concentration of 20 IU/mL. The results of this experiment show that there is no difference between the Baxter Fibrin sealant containing FXIII (experiment 2) and the Baxter Hyland-Immuno free of FXIII when submitted to the compaction text. Results obtained from the compaction tests show the same behavior for the FXIII free sealant. See FIG. 14.

A table summarizing the water retention data follows below.

TABLE 1

| Sample # | Experiment # | % Water loss at 1000 rpm | % Water loss at 2000 rpm | % Water loss at 3000 rpm |
|---|---|---|---|---|
| 1 | 1 | 9.5 | 25 | 45 |
| 1 | 2A | 6 | 10 | 14 |
| 1 | 2B | not significant | 40 | 65 |
| 1 | 4 | 4.2 | 9.4 | 14.3 |
| 2 | 1 | 18 | 40 | 70 |
| 2 | 2A | 10 | 21 | 35 |
| 2 | 2B | not significant | 40 | 65 |
| 2 | 4 | not significant | 15 | 22 |
| 3 | 1 | 20 | 40 | 80 |
| 3 | 2A | 11 | 20 | 35 |
| 3 | 2B | not significant | 40 | 65 |
| 3 | 4 | not significant | 23 | 34 |
| 4 | 1 | 20 | 72 | 90 |
| 4 | 2A | 11 | 20 | 35 |
| 4 | 2B | not significant | — | 80 |
| 4 | 4 | 14 | 24 | 34 |

It has been postulated that ionic strength of thrombin regulates the pore size of fibrin clot structure. By using high ionic strength thrombin solutions one can achieve a fibrin clot having a smaller pore size than with lower concentration thrombin solutions. The present example demonstrates a method for fabricating a fibrin clot material where the concentration does not govern the pore size of the fibrin clot. As set forth above, by using a chelating agent to bind to calcium, calcium concentration does not affect the pore size. Even when a 4 IU/mL thrombin concentration and 250 IU/mL thrombin concentration was used, the resulting fibrin material had substantially the same pore size. Ionic strength was measured with an osmometer and correlated with the measurement of the turbidity at 800 nm with a spectrophotometer. Observation of the sample network structure was accomplished by scanning electron microscopy. Table 2 below summarizes the correlation between final osmolarity of the fibrin samples and their respective optical densities. The results of this experiment illustrate that ionic strength, as demonstrated through osmolarity, does not regulate the structure of the fibrin clot.

Classic fibrin materials obtained by using water (0 mosm) as a diluent for fibrinogen and $CaCl_2$ for thrombin (4 IU/ml), for example, has a final osmolarity of 539 mosm. This is a result of fibrinogen reconstituted with water at a concentration of 90 mg/ml (610 mosm) combined with thrombin constituted with $CaCl_2$ at a kit concentration of 4 IU/ml (468 mosm). The resulting classic fibrin material is opaque white with an optical density of 2.8 AUFS when measured with a spectrophotometer at 800 nm.

Fibrin materials produced with PBS (286 mosm) have a final osmolarity of 445 mosm. This is a result of fibrinogen reconstituted and diluted with PBS at a concentration of 25 mg/ml (588 mosm) combined with thrombin reconstituted and diluted with PBS at a concentration of 10 IU/ml (315 mosm). The resulting fibrin material is optically clear with an optical density of 0.5 AUFS when measured with a spectrophotometer at 800 nm.

Fibrin materials produced with a citrate buffer at 0.033 M (100 mosm) have a final osmolarity of 224 mosm. This is a result of fibrinogen reconstituted and diluted with citrate at a concentration of 50 mg/ml (336 mosm) combined with thrombin reconstituted and diluted with citrate at a concentration of 20 IU/ml (112 mosm). The resulting fibrin material is optically clear with an optical density of 0.45 AUFS when measured with a spectrophotometer at 800 nm. The fibrin hydogel material in this experiment is clear and composed of thin fibers with an ionic strength of less than 300 mosm, which is considered to be the physiological level. Fibrin obtained by mixing fibrinogen at 12.5 mg/ml with thrombin at 10 IU remains clear (0.8 AUFS) with an osmolarity of 167 mosm.

Fibrin materials produced with a citrate buffer at 0.066 M (190 mosm) have a final osmolarity of 317 mosm. This is a result of fibrinogen reconstituted and diluted with citrate at a concentration of 50 mg/ml (435 mosm) combined with thrombin reconstituted and diluted with citrate at a concentration of 20 IU/ml (200 mosm). The resulting fibrin material is optically clear with an optical density of 0.23 AUFS when measured with a spectrophotometer at 800 nm. The fibrin hydogel material in this experiment is also clear and composed of thin fibers with an ionic strength of less than 300 mosm, which is considered to be the physiological level. Fibrin obtained by mixing fibrinogen at 12.5 mg/ml with thrombin at 10 IU remains clear (0.5 AUFS) with an osmolarity of 260 mosm.

TABLE 6

| Buffer | Final Osmolarity of Fibrin Material (mosm) | Optical Density (AUFS at 800 nm) |
| --- | --- | --- |
| Water (CaCl$_2$) | 539 | 2.8 |
| PBS | 451 | 0.255 |
| Citrate (0.033 M) | 224 | 0.45 |
| Citrate (0.066 M) | 317 | 0.23 |

The buffers also play an active role in the permeability, fiber diameter, and mass length ratio of the fibrin material. Significant differences can be observed between PBS and NaCl (0.15 M). These buffers have the same osmolarity, yet their effects on fibrin materials are markedly different. See Table 3 below. For a thrombin concentration of 2 IU/mL reconstituted with NaCl at 0.15 M, the permeability of the fibrin is $30.6 \times 10^{-12}$ at a fibrinogen concentration of 25 mg/ml and $136 \times 10^{-12}$ at a fibrinogen concentration of 12.5 mg/ml. Using PBS as a buffer yields a fibrin permeability of $6.9 \times 10^{-12}$ at a fibrinogen concentration of 25 mg/ml and $39.5 \times 10^{-12}$ at a fibrinogen concentration of 12.5 mg/ml. This experiment demonstrates that the fibrin material utilizing PBS as a buffer is nearly five times less permeable than classic fibrin materials, thus capable of retaining more water. The diameters of fibers are also affected by the buffer selected. For a thrombin concentration of 2 IU/ml diluted with NaCl at 0.15 M, the fibers have a diameter of 0.107 μm at a fibrinogen concentration of 25 mg/ml and 0.14 μm at a fibrinogen concentration of 12.5 mg/ml. Using PBS as a buffer yields fibers with a diameter of 0.051 μm at a fibrinogen concentration of 25 mg/ml and 0.075 μm at a fibrinogen concentration of 12.5 mg/ml. Additionally, the mass length ratio is also affected by the buffer selected to reconstitute the fibrinogen and thrombin. At a thrombin concentration of 2 IU/ml buffered with NaCl at 0.15 M, the mass length ratio is $8.1 \times 10^{12}$ at a fibrinogen concentration of 25 mg/ml and $13.9 \times 10^{12}$ at a fibrinogen concentration of 12.5 mg/ml. The use of PBS as a buffer yields fibers with a mass length ratio of $1.83 \times 10^{12}$ at a fibrinogen concentration of 25 mg/ml and $4.03 \times 10^{12}$ at a fibrinogen concentration of 12.5 mg/ml, a four-fold reduction under NaCl at 0.15 M.

For a thrombin concentration of 250 IU/ml (Table 4) diluted with NaCl at 0.15 M, the permeability of the fibrin is $14.24 \times 10^{-12}$ at a fibrinogen concentration of 25 mg/ml and $47.7 \times 10{-12}$ at a fibrinogen concentration of 12.5 mg/ml. Using PBS as a buffer yields a fibrin permeability of $8.9 \times 10^{-12}$ at a fibrinogen concentration of 25 mg/ml and $41 \times 10^{-12}$ at a fibrinogen concentration of 12.5 mg/ml. This experiment demonstrates that the fibrin material utilizing PBS as a buffer is less permeable than classic fibrin materials, thus capable of retaining more water. The diameters of fibers are also affected by the buffer selected. For a thrombin concentration of 250 IU/ml diluted with NaCl at 0.15 M, the fibers have a diameter of 0.073 μm at a fibrinogen concentration of 25 mg/ml and 0.083 μm at a fibrinogen concentration of 12.5 mg/ml. Using PBS as a buffer yields fibers with a diameter of 0.057 μm at a fibrinogen concentration of 25 mg/ml and 0.077 μm at a fibrinogen concentration of 12.5 mg/ml. Additionally, the mass length ratio is also affected by the buffer selected to reconstitute the fibrinogen and thrombin. At a thrombin concentration of 250 IU/ml buffered with NaCl at 0.15 M, the mass length ratio is $3.78 \times 10^{12}$ at a fibrinogen concentration of 25 mg/ml and $4.83 \times 10^{12}$ at a fibrinogen concentration of 12.5 mg/ml. The use of PBS as a buffer yields fibers with a mass length ratio of $2.36 \times 10^{12}$ at a fibrinogen concentration of 25 mg/ml and $4.24 \times 10^{12}$ at a fibrinogen concentration of 12.5 mg/ml.

These experiments illustrate that the type of buffer used, differently effects the permeability factor as shown for NaCl and PBS (Tables 3 and 4). These experiments demonstrate that the concentration of thrombin has no effect on the permeability factor, fiber diameter, and mass length ratio as well when PBS, and not NaCl, is the buffer. PBS is an admixture composed of 0.13 M NaCl (800 mg/L), KCL (20 mg/L), anhydrous Na$_2$HPO$_4$ (115 mg/L), and KH$_2$PO$_4$. Thus, PBS buffer contains NaCl at a molarity of nearly the NaCl 0.015 M buffer described in Tables 3 and 4. As the data shows phosphate is therefore the complexing agent of the endogenous calcium. Tables summarizing these experiments are labeled Table 7 and Table 8 below.

TABLE 3

Thrombin 2 IU/ml

| Buffer | Fibrinogen Concentration | Permeability (K$_s$) | Fiber Diameter μm | mass length ratio |
| --- | --- | --- | --- | --- |
| NaCl 0.15 M | 25 mg/ml | $30.6 \times 10^{-12}$ | 0.107 | $8.1 \times 10^{12}$ |
| PBS | 25 mg/ml | $6.9 \times 10^{-12}$ | 0.051 | $1.83 \times 10^{12}$ |
| NaCl 0.15 M | 12.5 mg/ml | $136 \times 10^{-12}$ | 0.14 | $13.9 \times 10^{12}$ |
| PBS | 12.5 mg/ml | $39.5 \times 10^{-12}$ | 0.075 | $4.03 \times 10^{12}$ |

TABLE 4

Thrombin 250 IU/ml

| Buffer | Fibrinogen Concentration | Permeability (K$_s$) | Fiber Diameter μm | mass length ratio |
| --- | --- | --- | --- | --- |
| NaCl 0.15 M | 25 mg/ml | $14.24 \times 10^{-12}$ | 0.073 | $3.78 \times 10^{12}$ |
| PBS | 25 mg/ml | $8.9 \times 10^{-12}$ | 0.057 | $2.36 \times 10^{12}$ |
| NaCl 0.15 M | 12.5 mg/ml | $47.7 \times 10^{-12}$ | 0.083 | $4.83 \times 10^{12}$ |
| PBS | 12.5 mg/ml | $41 \times 10^{-12}$ | 0.077 | $4.24 \times 10^{12}$ |

Calculation for permeability (Ks):

$$\frac{\text{Flow (ml/sec)} \times \text{time to clot} \times \text{viscosity} (10^2)}{\text{Pressure} \times \text{Surface area of clot}}$$

Calculation for fiber diameter:

$$D^2 = 44.1 \times Ks \times \text{concentration of fibrinogen} (X^{1.3736})$$

Calculation for mass length ratio:

$$\mu = \times D^2 \times C/4X, \text{ where } C=4.36 \text{ g/cm}^3$$

Figure 9:
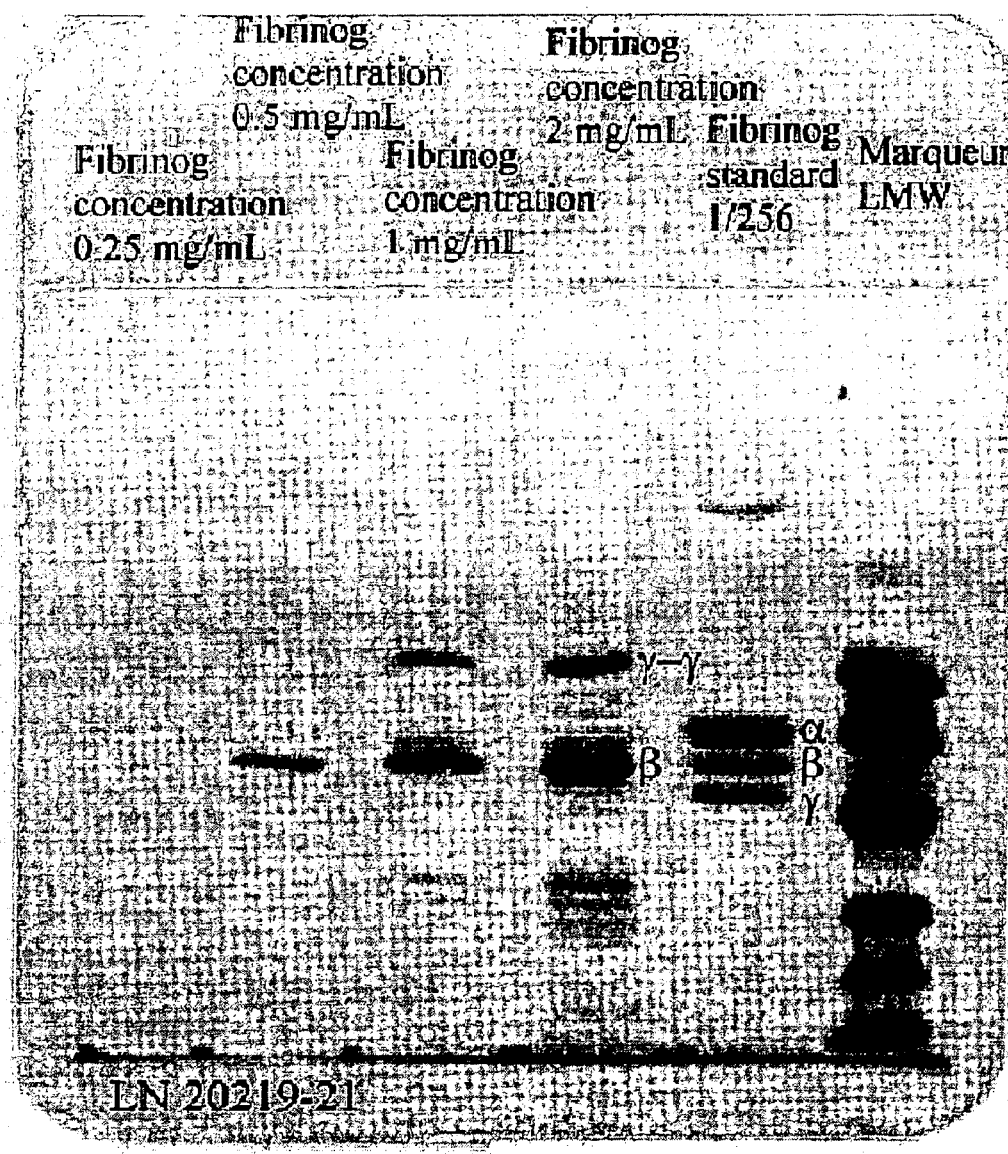
FIG. 9 depicts a classic fibrin material in gel electrophoresis.
Figure 10:
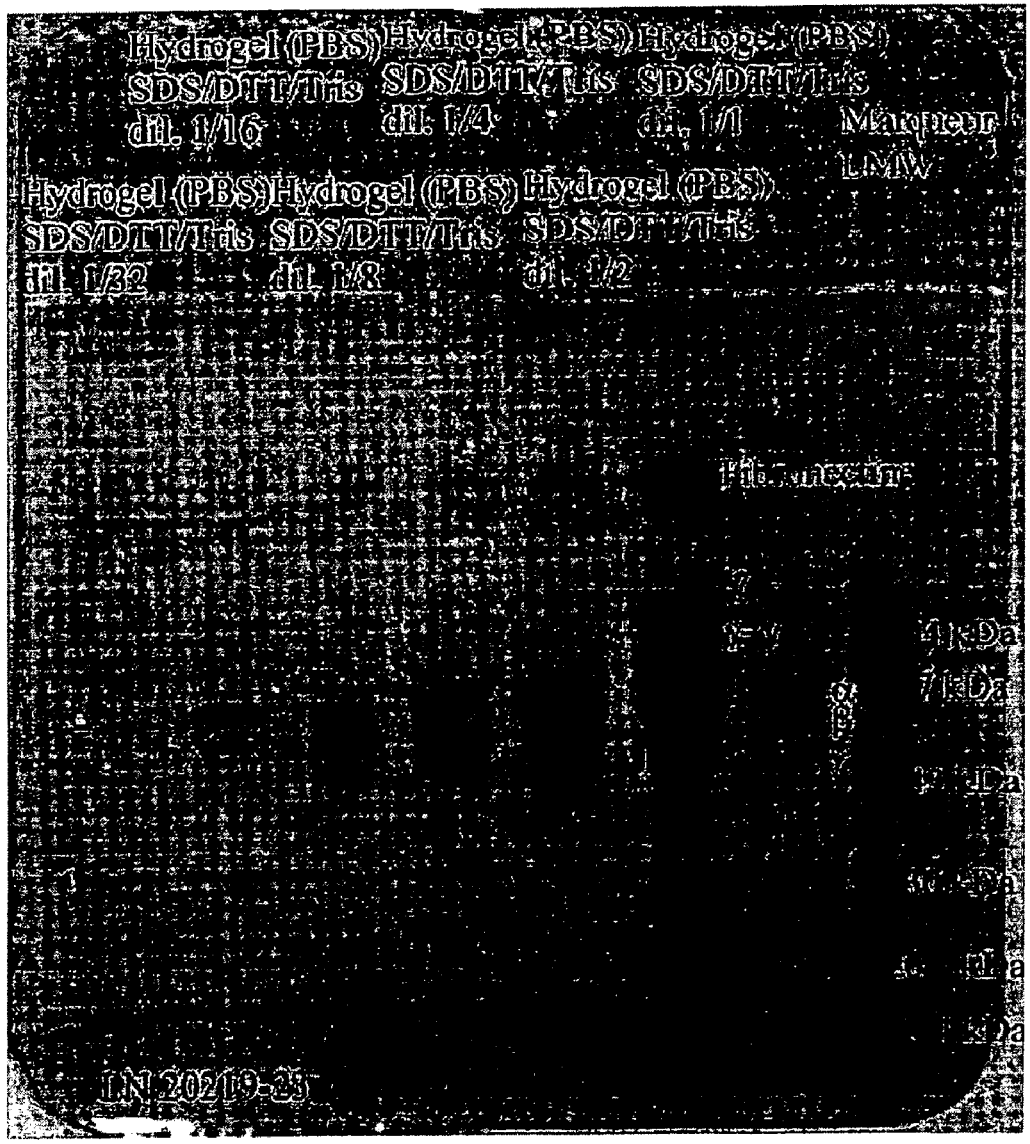
FIG. 10 depicts a fibrin hydrogel material in gel electrophoresis.

The role of PBS as a complexing agent can also be seen by gel electrophoresis studies of fibrin materials. When an electric current is applied to an SDS-polyacrylimide-gelelectrophoresis containing fibrin hydrogel material prepared with PBS, little or no gamma-gamma banding can be seen while a fibronectin band may be viewed. This demonstrates that the PBS complexes calcium so that calcium is not available to collaterally associate fibrin through cross-linking. Classic fibrin materials show distinctive, strong gamma-gamma band, and no fibronectin band, when prepared with water or NaCl as a buffer. NaCl buffer with a molarity of 0.15 cannot block the action of calcium. The NaCl buffer's inability to block the action of calcium allows calcium to play its traditional role in collaterally associating fibrin, thus allowing thrombin to affect the pore size of the fibrin material. By acting as a complexing agent for endogenous calcium, PBS substantially removes thrombin's ability to affect pore size. FIG. 9 below illustrates the classic fibrin material in gel electrophoresis. FIG. 10 below illustrates the fibrin hydrogel material in gel electrophoresis.

The fibrin hydrogel materials have also been determined to contain anti-adhesive properties. Tables 5 and 6 below illustrate the anti-adhesive properties of the fibrin hydrogel materials. Table 9 shows the results of a side model study on rats. The caecum and interfacing parietal wall were abraded sufficiently to cause bleeding. The bleeding surfaces were cauterized to stop the bleeding on the injured surfaces in both control and test animals. Two types of fibrin hydrogel materials were formed between the injured surface. Fibrin film 1 (FF1) differs from fibrin film 2 (FF2) in that FF2 was compressed to release some water. The results show that the wounds treated with either normal fibrin hydrogel material (FF1) or compressed fibrin hydrogel material (FF2) have no adhesions between the caecum surface and the parietal surface. The control group for Table 5 had no fibrin hydrogel material applied, resulting in level 3 (the most severe) adhesions between the caecum surface and the parietal surface.

Table 6 shows the anti-adhesion properties of hydrogel fibrin glue material. This hydrogel material polymerizes within the body of the animal upon application using a delivery device such as that shown in FIG. 6. The fibrin hydrogel glue was applied directly to the would on the caecum surface, as well as to the parietal surface. All animals that received this fibrin hydrogel glue treatment were free of adhesion. In a second trial, a precast fibrin hydrogel material was positioned between injured surfaces. Using a pre-cast fibrin hydrogel material demonstrated significant anti-adhesion properties as well.

TABLE 5

| Animal | Product Applied | Result |
| --- | --- | --- |
| Control Rat 1 | none | adhesion (level 3) |
| Control Rat 2 | none | adhesion (level 3) |
| Control Rat 3 | none | adhesion (level 3) |
| Control Rat 4 | none | adhesion (level 3) |
| Rat 1 | FF1 | no adhesion |
| Rat 2 | FF1 | no adhesion |
| Rat 3 | FF2 | no adhesion |
| Rat 4 | FF2 | no adhesion |

TABLE 6

| Group Type | Number of Individuals | Thrombin Concentration | Result |
| --- | --- | --- | --- |
| Control | 5 | — | adhesion (level 3) |
| Pre-cast Hydrogel Fibrin Film | 5 | 100 IU/ml | 20% adhesion |
| Hydrogel Fibrin Glue | 5 | 100 IU/ml | 0% adhesion |

While the specific embodiments have been illustrated and described, numerous modifications come to mind without significantly departing from the spirit of the invention and the scope of protection is only limited by the scope of the accompanying claims.

We claim:

1. A fibrin hydrogel material comprising:
   a fibrin material, wherein the hydrogel material having has a water content of at least 90% by weight of the hydrogel material and whereby the hydrogel material retains from about 80% to about 90% of the water upon compression by a force from about 1 psi to about 14 psi.

2. The fibrin hydrogel material of claim 1 wherein fibrin hydrogel material has a pore size within the range of from about 0.1 μm to about 5.0 μm.

3. A fibrin hydrogel material comprising: a fibrin material, wherein the hydrogel material has a water content of at least 90% by weight of the hydrogel material and whereby the hydrogel material retains from about 80% to about 50% of the water upon compression by a force from about 1 psi to about 14 psi wherein the fibrin hydrogel material is produced using an essentially calcium free thrombin solution.

4. The fibrin hydrogel material of claim 1 having an optical clarity of less than about 1.0 AUFS when measured with a spectrophotometer at 800 nm.

5. The fibrin hydrogel material of claim 1 substantial free of gamma-gamma cross-linking, as determined through gel electrophoresis.

6. The fibrin hydrogel material of claim 1 having anti-adhesive properties.

7. A method for producing a fibrin hydrogel material of claim 1, the method comprising the steps of:
   providing a fibrinogen reagent;
   providing a calcium chelating agent;
   providing a catalyst reagent essentially free of calcium; and
   mixing the fibrinogen, the chelating agent, and the catalyst to form the fibrin hydrogel material.

8. The method of claim 7 wherein the fibrinogen reagent comprises fibrinogen carried in a first diluent.

9. The method of claim 8 wherein the first diluent is a phosphate buffered saline solution.

10. The method of claim 9 wherein fibrinogen has a concentration from about 1.5 mg/ml to about 100 mg/ml.

11. The method of claim 7 wherein the catalyst reagent comprises thrombin.

12. The method of claim 11 wherein the catalyst reagent comprises thrombin carried in a second diluent.

13. The method of claim 12 wherein the second diluent is a phosphate buffered saline solution.

14. The method of claim 11 wherein thrombin has a concentration from about 1 IU/ml to about 1000 IU/ml.

15. The method of claim 7 wherein the chelating agent is EGTA.

16. The method of claim 7 wherein the chelating agent is EDTA.

17. The method of claim 7 wherein the chelating agent is citrate.

18. The method of claim 7 wherein the fibrin hydrogel material car be fabricated into articles selected from the group consisting of fins, tubes, and pellets.

19. The method of claim 18 wherein the fibrin hydrogel material can be fabricated into articles using techniques selected from the group of extrusion, molding and thermal forming.

20. The method of claim 18 wherein the fibrin hydrogel material can be sterilized at a temperature below 0° C. by gamma radiation, stored at a temperature below 0° C., and used upon demand.

21. The method of claim 19 wherein the sterilization by gamma radiation is below 25° C., at a dosage of at least 25 kGy.

22. A multiple layer fibrin material comprising:
a fibrin glue layer; and
a fibrin hydrogel layer, the fibrin hydrogel being capable of retaining from at least about 80% to about 90% of water by weight of the hydrogel when compressed by a force of 1–14 psi, and having relatively no cross-linking.

23. The multiple layer fibrin material of claim 22 wherein the fibrin glue layer has a pore size from about 2 $\mu$m to about 10 $\mu$m.

24. The multiple layer fibrin material of claim 22 wherein the fibrin hydrogel layer has a pore size from about 0.1 $\mu$m to about 5 $\mu$m.

25. The multiple layer fibrin material of claim 22 further including a fibrin layer, and being substantially cross-linked.

26. The multiple layer fibrin material of claim 25 wherein the fibrin hydrogel layer has a pore size from about 0.1 $\mu$m to about 5 $\mu$m.

27. The multiple layer fibrin material of claim 22 wherein the multiple layer fibrin material has anti-adhesive properties.

28. A multiple layer fibrin material for treating a patient comprising:
a fibrin film layer; and
a fibrin hydrogel layer, the fibrin hydrogel having a water content of at least 90% by weight of the fibrin hydrogel and whereby the fibrin hydrogel retains from about 80% to about 90% of the water upon compression by a force from about 1 psi to about 14 psi.

29. The multiple layer fibrin material of claim 28 wherein the multiple layer fibrin material has anti-adhesive properties.

30. The multiple layer fibrin material of claim 28 wherein the fibrin film layer has a pore size from about 2 $\mu$m to about 10 $\mu$m.

31. The multiple layer fibrin material of claim 28 wherein the fibrin hydrogel layer has a pore size from about 0.1 $\mu$m to about 5 $\mu$m.

32. The multiple layer fibrin material of claim 28 further including a therapeutic fibrin hydrogel layer.

33. The multiple layer fibrin material of claim 32 wherein the therapeutic fibrin hydrogel layer has a pore size from about 0.1 $\mu$m to about 5 $\mu$m.

34. The multiple layer fibrin material of claim 28 whereby the retained water comprises a releasably retained diluent.

35. The multiple layer fibrin material of claim 34 whereby the releasably retained diluent is selected from the group consisting of antibiotics, fibrinolytic agents and biological response modifiers.

36. The multiple layer fibrin material of claim 35 whereby the therapeutic agent comprises a pharmaceutical compound.

37. The multiple layer fibrin material of claim 35 whereby the therapeutic agent comprises living cells.

38. A multiple layer fibrin material for treating a patient comprising:
a fibrin film layer;
a therapeutic fibrin hydrogel layer, the fibrin hydrogel having a water content of at least 90% by weight of the fibrin hydrogel and whereby the fibrin hydrogel retains from about 80% to about 90% of the water upon compression by a force from about 1 psi to about 14 psi; and
a fibrin glue layer attaching the fibrin film layer to the fibrin hydrogel layer.

39. The multiple layer fibrin material of claim 38 wherein the fibrin film layer has a pore size form about 2 $\mu$m to about 10 $\mu$m.

40. The multiple layer fibrin material of claim 38 wherein the multiple layer fibrin material has anti-adhesive properties.

41. The multiple layer fibrin material of claim 38 wherein the therapeutic fibrin hydrogel has a pore size from about 0.1 $\mu$m to about 5 $\mu$m.

42. The multiple layer fibrin material of claim 38 whereby the retained water comprises a releasably retained diluent.

43. The multiple layer fibrin material of claim 42 whereby the releasably retained diluent comprises a therapeutic agent.

44. The multiple layer fibrin material of claim 43 whereby the therapeutic agent is selected from the group consisting of antibiotics, fibrinolytic agents and biological response modifiers.

45. The multiple layer fibrin material of claim 43 whereby the therapeutic agent comprises living cells.

* * * * *